(12) United States Patent
Matthys

(10) Patent No.: US 9,050,142 B2
(45) Date of Patent: Jun. 9, 2015

(54) ANGULARLY STABLE DEVICE FOR MUTUALLY FIXING A LONGITUDINAL CARRIER WITH A BONE FIXATION ELEMENT

(75) Inventor: Romano Matthys, Fideris (CH)

(73) Assignee: DePuy Synthes Products, Inc., Raynham, MA (US)

( * ) Notice: Subject to any disclaimer, the term of this patent is extended or adjusted under 35 U.S.C. 154(b) by 1617 days.

(21) Appl. No.: 11/814,203

(22) PCT Filed: Jan. 18, 2005

(86) PCT No.: PCT/CH2005/000023
§ 371 (c)(1),
(2), (4) Date: Mar. 18, 2008

(87) PCT Pub. No.: WO2006/076815
PCT Pub. Date: Jul. 27, 2006

(65) Prior Publication Data
US 2008/0208257 A1 Aug. 28, 2008

(51) Int. Cl.
*A61B 17/70* (2006.01)
(52) U.S. Cl.
CPC ......... *A61B 17/7035* (2013.01); *A61B 17/7049* (2013.01); *A61B 17/7041* (2013.01)
(58) Field of Classification Search
CPC .................................................. A61B 17/7049
USPC .......... 606/246–279; 403/384, 389, 391, 396, 403/398, 399
See application file for complete search history.

(56) References Cited

U.S. PATENT DOCUMENTS

| 4,920,959 | A | | 5/1990 | Witzel et al. |
| 5,290,288 | A | | 3/1994 | Vignaud et al. |
| 5,498,262 | A | * | 3/1996 | Bryan ........................... 606/252 |
| 6,106,527 | A | * | 8/2000 | Wu et al. ....................... 606/250 |

(Continued)

FOREIGN PATENT DOCUMENTS

| CH | 632658 | 10/1982 |
| DE | 195 34 136 | 3/1996 |

(Continued)

OTHER PUBLICATIONS

International Preliminary Report on Patentability, completed Dec. 29, 2006 for International Application No. PCT/CH2005/000023, filed Jan. 18, 2005.

(Continued)

*Primary Examiner* — Jerry Cumberledge
*Assistant Examiner* — Nicholas Plionis
(74) *Attorney, Agent, or Firm* — Baker & Hostetler LLP

(57) ABSTRACT

A device (1) for mutually fixing a longitudinal carrier (3) to a bone fixation element (4), wherein the device consists of a three-dimensional body (5) which has a channel (6) that is open on one side, wherein the axis of the channel (7) receives the longitudinal carrier (3), and a bore hole (8) that extends crosswise in relation to the axis of the channel (7) through the body (5) and that is provided with a wall (10). At least one part of the bore wall (10) disposed between the channel (6) and the bore hole (8) is embodied as an elastic element (11) which can be pressed into the region of the channel (6) by introducing the bone fixation element (4) into the bore hole (8), such that a longitudinal carrier (3) arranged in the channel can be firmly clamped in a rotational and longitudinal manner by said elastic element (11).

39 Claims, 3 Drawing Sheets

(56) References Cited

U.S. PATENT DOCUMENTS

| | | | |
|---|---|---|---|
| 6,117,135 A * | 9/2000 | Schläpfer | 606/250 |
| 6,206,881 B1 | 3/2001 | Frigg et al. | |
| 6,248,104 B1 | 6/2001 | Chopin et al. | |
| 6,273,914 B1 * | 8/2001 | Papas | 623/17.11 |
| 6,602,253 B2 * | 8/2003 | Richelsoph et al. | 606/252 |
| 2003/0028192 A1 * | 2/2003 | Schar et al. | 606/61 |
| 2003/0073996 A1 * | 4/2003 | Doubler et al. | 606/61 |
| 2004/0039385 A1 * | 2/2004 | Mazda et al. | 606/61 |

FOREIGN PATENT DOCUMENTS

| | | |
|---|---|---|
| DE | 19534136 | 3/1996 |
| FR | 2775587 | 9/1999 |
| JP | 2001299771 | 10/2001 |
| WO | WO 94/01049 | 1/1994 |
| WO | WO 95/13754 | 5/1995 |
| WO | WO 01/19267 | 3/2001 |
| WO | WO 2004/021901 | 3/2004 |

OTHER PUBLICATIONS

International Search Report, dated Aug. 4, 2006, in International Patent Application No. PCT/CH2005/000023.

Preliminary Rejection issued by Japanese Patent Office, Dated Jun. 3, 2009.

* cited by examiner

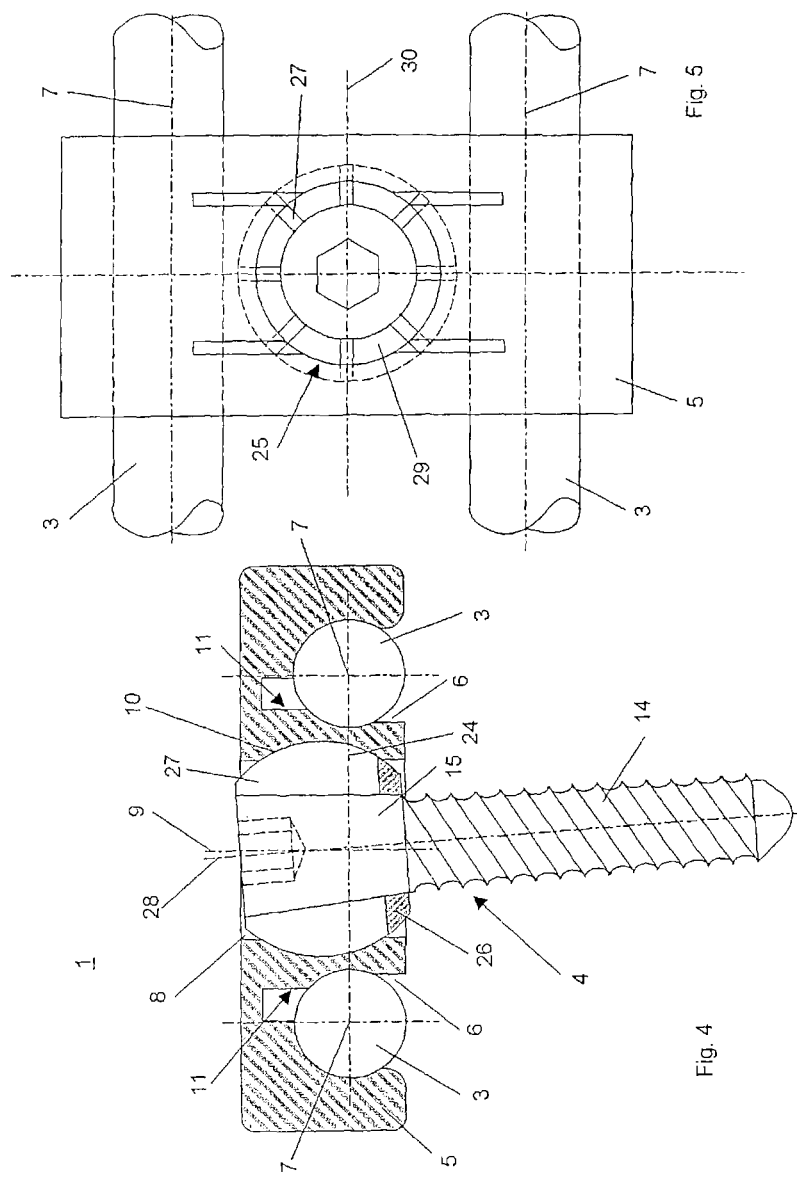

ANGULARLY STABLE DEVICE FOR MUTUALLY FIXING A LONGITUDINAL CARRIER WITH A BONE FIXATION ELEMENT

CROSS-REFERENCE TO RELATED APPLICATION

This Application is a national stage application under 35 U.S.C. 371 based on International Application Serial No. PCT/CH2005/000023 filed on Jan. 18, 2005 "ANGULARLY STABLE DEVICE FOR MUTUALLY FIXING A LONGITUDINAL CARRIER WITH A BONE FIXATION ELEMENT".

BACKGROUND OF THE INVENTION

1. Field of the Invention

The invention relates to a device of the introductory portion of claim 1.

With such devices, it is possible to connect an appropriate connecting rod or a longitudinal carrier, as used in spinal column surgery, over a bone fixation element, preferably a bone screw, with the bone, in order to obtain a rigid construction.

2. Description of the Related Art

U.S. Pat. No. 4,920,959 of WITZEL ET AL. discloses an external fixator, which is relatively cumbersome. In particular, the individual clamp elements must be brought into position on the rods.

The CH-A 632658 disclose an implant for fixing bones, for which the quality of the locking in position depends directly on the prestressing force, which can be realized between the Briden body and the bone. Here also, in the event that the implant is used as a clamp, the individual elements of the clamp must be brought into position on two parallel, longitudinal rods. Accordingly, a lateral mounting is not possible. In free-hand use, particularly in percutaneous and minimally invasive use, this may be difficult to realize and represents a major disadvantage.

On the other hand, open clamps are also known from U.S. Pat. No. 5,290,288 and the WO 94/01049 A1 as well as the French patent 2775587 A1. However, these open clamps all have the disadvantage that they require an additional element for their fixation. The holding device for the clamps, that is, the bone screw, must first of all be fixed in the bone and cannot be introduced freely selectively percutaneously in order to be able to position and fix the clamp thereon only then with the bone screw. For this reason, the longitudinal carrier can be placed on the bone screw only after the clamp is positioned.

Finally, the WO95/13754 discloses a clamp, for which the longitudinal rod can be introduced laterally into the open channel of a clamp and clamped tightly there by means of a clamping screw, which can be passed through the clamp. However, the clamping screw has only this one function and is not constructed as a bone screw, which could fasten the whole construction to the bone. The same is true also for the holding device known from the DE-A 195 34 136.

The devices, known from the prior art, accordingly are quite complicated generally.

SUMMARY OF THE INVENTION

The invention is to provide a remedy here. It is an object of the invention to provide a device, which is very simple in construction, can be used very flexibly and permits a minimally invasive surgical technique.

Pursuant to the invention, this objective is accomplished with a device, which has the distinguishing features of claim 1.

The advantages of the inventive device are manifold and can be described as follows:
the device is a single part;
the longitudinal carrier can be introduced previously into the device in pre-shaped, whereas the bone screws have to be set only when their exact position is known;
the device can be used at a fixator as well as in at internal fixator;
if the longitudinal carrier must be fixed with a further device to the spinal column, such a further device can be slipped simply onto the longitudinal carrier without having to be pushed laboriously over the length of the longitudinal carrier and
before the bone fixation elements are set, the longitudinal carrier can be introduced into the human body, so that it is easy for the surgeon to determine the position of the bone fixation elements, which are to be fastened subsequently to the vertebrae.

The inventive device permits a longitudinal carrier, corresponding to the recess, and a standard head locking screw to be accommodated. When the head locking screw is tightened, the longitudinal carrier is blocked in the inventive device.

Further advantageous developments of the invention are characterized in the dependent claims.

In a preferred embodiment, the elastic, resilient or spring-like element is separated partly from the body by at least two slots, which penetrate into the body from the borehole wall transversely to the channel axis. The advantages of this configuration are to be seen essentially therein that the resilient element can be constructed in one piece with the body, so that parts cannot be lost and it becomes possible to produce the device simply.

In a further embodiment, the resilient element is constructed in a cross-sectional surface, orthogonal to the channel axis, as a hook-shaped segment of the body and has a free end. The advantage of this embodiment lies therein that the hook-shaped construction of the resilient element enables the longitudinal carrier to be fixed rigidly in the channel.

In a further embodiment, the channel is constricted by the free end of the resilient element, so that a longitudinal carrier can be snapped into the channel. The advantage of this configuration lies essentially therein that the longitudinal carrier is also held in the channel, when it is not fixed in the channel by the tightening of the bone fixation element.

In a further embodiment, the borehole is constructed at least partly conically. The advantages of this configuration are to be seen essentially therein that the resilient element can be pressed easily into the region of the channel by means of a conical connection between the borehole and the bone fixation element, so that no further parts are required for fixing the longitudinal carrier in the channel.

In a further embodiment, the borehole has an internal thread. The advantages of this construction lie therein that, due to the thread connection between the borehole and a bone fixation element, it is possible to achieve a rigid connection between the body and the bone fixation element.

In a further embodiment, the borehole at least partly has a spherically concave wall. Furthermore, a complementary spherical radial resilient deformable clamping element, with a central borehole suitable for accommodating the bone fixation element, is supported pivotably in the cavity and can be blocked releasably. The advantages of this configuration are to be seen essentially therein that the bone fixation element, before the device is locked in the borehole, is mounted polyaxially pivotably, so that it is possible to fix the bone fixation element at different angles relative to the body.

In a further embodiment, the borehole has two, longitudinal conical sections, each longitudinal conical section expanding in the direction of the mouth of the borehole. The advantages of this configuration lie therein that the device can be implanted either with a channel, open towards the rear, so that the longitudinal carrier can be placed in the device after the bone fixation agent is set, or the device may be implanted with a channel, open at the front, so that, to begin with, the longitudinal carrier can be brought into the human body and that subsequently the necessary number of devices and bone fixation elements can be implanted and fixed.

In a further embodiment, the channel, viewed in a cross-section orthogonal to the channel axis, has a polygonal transverse surface. The advantages of this configuration lie therein that the longitudinal carrier can be connected rotationally stably with the device.

Two different surgical methods for the inventive device are described briefly below.

Surgical Method A:

A) the longitudinal carrier is first of all brought by a stab incision into the region of the patient, which is to be treated, and pushed percutaneously into the desired position;

B) the surgeon can now control the contour of the longitudinal carrier and correct it simply;

C) once the longitudinal carrier has the desired contour, the desired number of devices (clamps) can be introduced through appropriate stab incisions percutaneously and brought directly laterally onto the rod;

D) subsequently, the holes for the head locking screws are drilled;

E) the angularly stable head locking screws are now screwed into the boreholes of the clamps, but not yet tightened;

F) if the setting is correct, the angularly stable head locking screws are tightened definitively, so that the construction, formed from the longitudinal carrier, the clamps and the bone screws, becomes rigid and the fracture is fixed.

Surgical Method B:

1. the inventive device (clamp) is positioned with the posterior open channel relative to the desired bone part;

2. a head locking screw is screwed through the conical borehole of the clamps to a specified depth, so that the clamp is pre-fixed;

3. the longitudinal carrier is shaped to correspond to anatomical requirements;

4. the longitudinal carrier is inserted into the open channel of the already pre-mounted clamp;

5. the head locking screw is now tightened completely in the clamp, so that the longitudinal carrier is fixed at the clamp;

6. the fracture is set over the longitudinal carrier with a suitable setting instrument;

7. the set bone fragments are fixed by means of the clamps;

8. optionally, the bone fixation construction is supplemented with clamps.

BRIEF DESCRIPTION OF THE DRAWINGS

The invention and further developments of the invention are explained in even greater detail in the following by means of the partially diagrammatic representations of several examples. In the drawing

FIG. 4 shows a section through a further embodiment of the inventive device and FIG. 5 shows a plan view of the embodiment, shown in FIG. 4, of the inventive device.

DETAILED DESCRIPTION OF THE CERTAIN EMBODIMENTS

Figure 1:
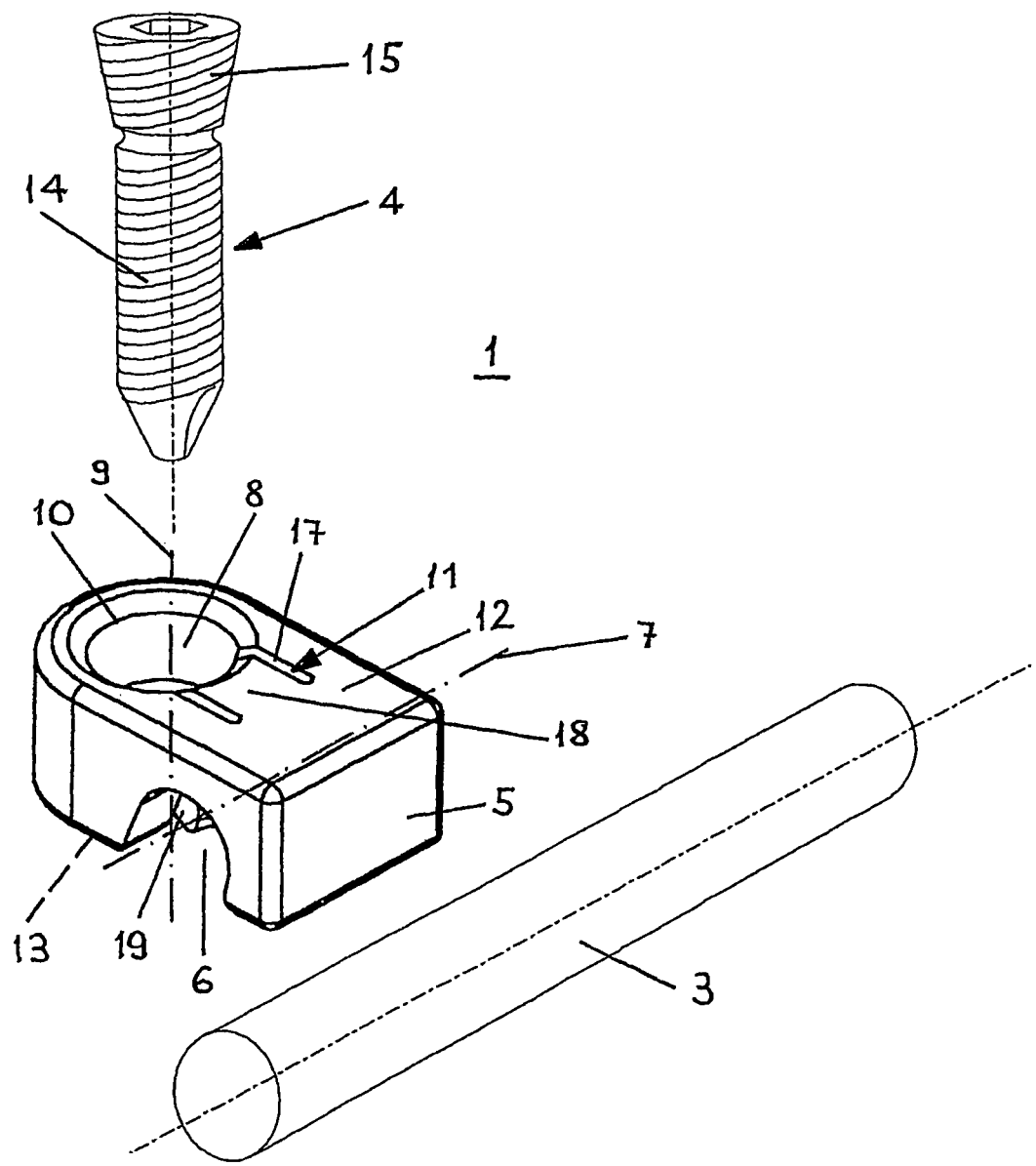
FIG. 1 shows an exploded representation of a bone fixation device with a longitudinal carrier, an embodiment of the inventive device (clamps) and a bone screw.
Figure 2:
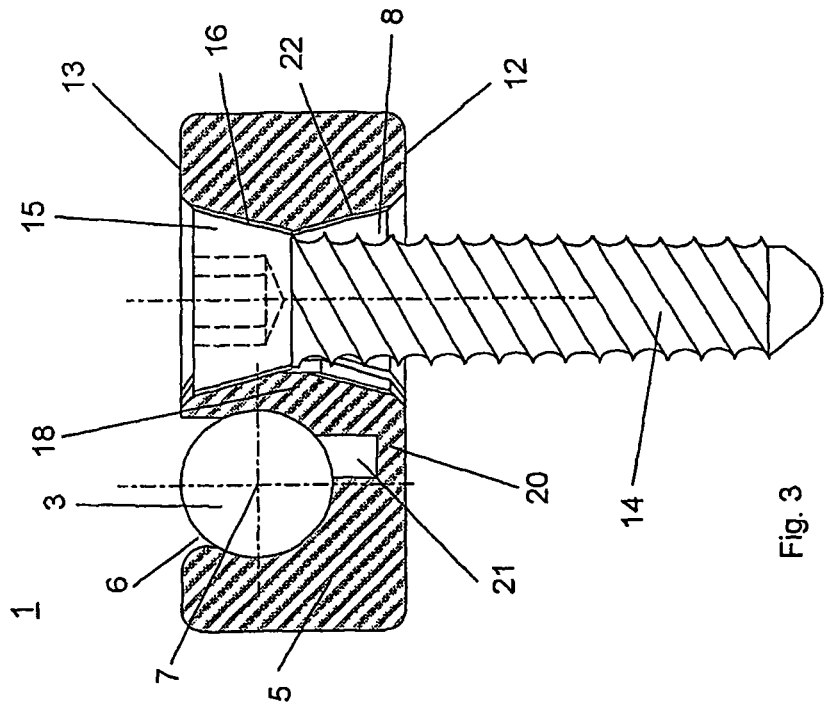
FIG. 2 shows a section through the embodiment, shown in FIG. 1, of the inventive device with a bone screw, introduced from the first surface, and a longitudinal carrier.

FIG. 1 shows an embodiment of the device 1 together with a bone fixation element 4, constructed as a bone screw, and a longitudinal carrier 3, the device 1 comprising essentially a 3-dimensional body 5 with a first surface 12 and, parallel thereto, a second surface 13. The three-dimensional body 5 serves as an element connecting the longitudinal carrier 3 and the bone fixation element 4 and comprises a borehole 8 with a borehole axis 9, which passes through the three-dimensional body 5 from the first surface 12 to the second surface 13 and is suitable for accommodating the bone fixation element 4. Furthermore, a channel 6, which is open towards the second surface 13, has an axis 7, which is perpendicular to the borehole axis 9 and is open in the direction of the second surface 13, so that a longitudinal carrier 3 can be introduced into the channel 6 transversely to the bone fixation element 4, passes through the three-dimensional body 5. The borehole 8 and the channel 6 are disposed in such a manner, that they do not intersect. Furthermore, the three-dimensional body 5 comprises a hook-shaped segment 18, which is limited by two slots 17 penetrating from the borehole 8 perpendicularly to the channel axis 7 into the body 5, can be deformed resiliently because of the slots 17 extending from the first to the second surface 12; 13 and forms the elastic element 11 for fixing the longitudinal carrier 3 in the channel 6. In the region of the hook-shaped segment 18, the channel 6 encloses the longitudinal carrier 3 with a contact angle $\alpha$ of more than 180° (FIG. 2). As the screw shaft of the bone fixation element 4, constructed as a bone screw, is being screwed in, the hook-shaped segment 18 is formed by the conical head 15 of the bone fixation element 4 in such a manner, that the free end 19 of the hook-shaped segments 18 is pressed against the longitudinal carrier 3, which has been introduced into the channel 6, and this longitudinal carrier 3 is fixed rotationally and longitudinally in channel 6.

Figure 3:
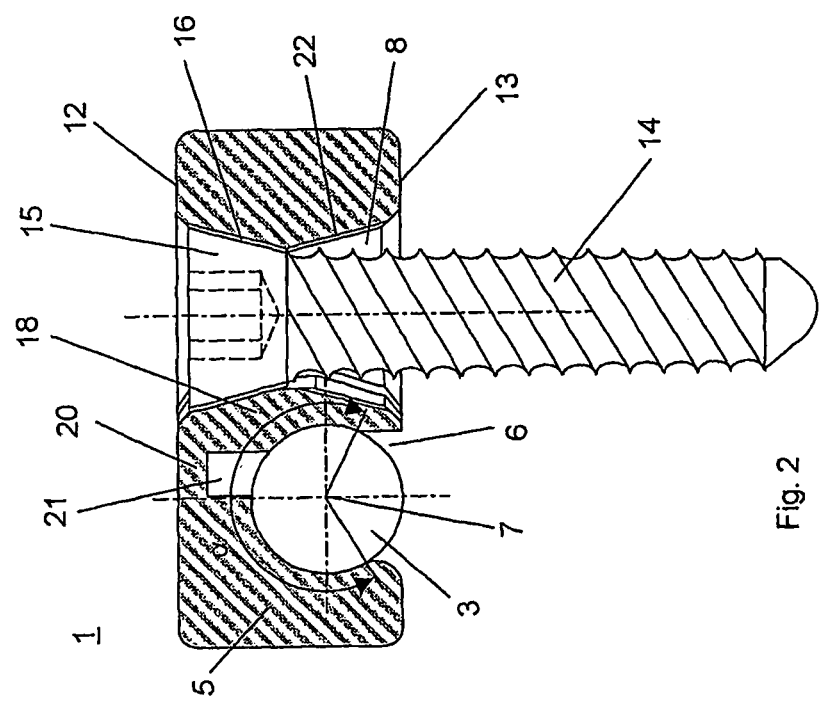
FIG. 3 shows a section through the embodiment, shown in FIG. 1, of the inventive device with a bone screw, introduced from the second surface, and a longitudinal carrier.

As can be seen from FIGS. 2 and 3, the channel 6 has a notch 21, which penetrates parallel to the axis 7 of the channel 6, so that a resiliently deformable strip, forming the fixed end 20 of the hook-shaped segment 18, remains between the base of the notch and the first surface 12. The borehole 8 has two conical longitudinal sections, which expand conically in each case in the direction of the first surface 12 and in the direction of the second surface 13 respectively. On each of the conical longitudinal sections, the borehole 8 has a conical internal thread 22, which can be brought into an engagement with the conical external thread 16 at the conical head 15, so that the bone screw 14 can be fixed rigidly in the three-dimensionally body 5. Because of the two conical longitudinal sections of the borehole 8, the possibility exists of introducing the bone fixation element 4 from the first or from the second surface 12; 13, depending on the application, into the three-dimensionally body 5. With this, the possibility is also provided of implanting the three-dimensional body 5 in such a manner, that the longitudinal carrier 3 can be introduced from the side (FIG. 3), directed towards the head 15, or from the side (FIG. 2), averted from the head 15 of the three dimensional body 5 into the channel 6.

The device, shown in FIGS. 4 and 5, differs from the embodiment, shown in FIGS. 1 to 3, in that a) it comprises two channels 6, the axes 7 of which extend parallel to one another. A plane of symmetry 30, which is perpendicular to a straight line intersecting the channel axes 7 orthogonally and halves these straight, connecting lines 24, is disposed between the channel axes 7. The configuration of the second channel 6 is the mirror image with respect to the plane of symmetry 30. The two elastic elements 11 are also constructed in mirror image fashion to the plane of symmetry 30;

b) the wall 10 of the borehole 7 is constructed spherically concavely. The conical head 15 of the bone fixation element 4, which is constructed as a bone screw 14, tapers in the direction of the screw shaft 14 and is introduced in a complementary central conical borehole 26 of a tensioning element 25, which is supported in the borehole 7 and can be deformed resiliently in the radial direction so that, as the bone fixation element 4, which is constructed as a bone screw, is tightened, the resilient tensioning element 25 is expanded, as a result of which the elastic element 11 is pressed against the longitudinal carrier 3, which has been introduced into the channels 6, and the device is blocked. The resilient deformability of the tensioning element 25 is achieved by eight notches 27, which penetrate the wall 29 of the tensioning element 25 on a portion of their length parallel to the longitudinal axis 28 of the central borehole 26 and on a portion of their length. This configuration with at least one partially spherical wall 10 of the borehole 7 and the complementary tensioning element 25 permits the bone fixation element 4 to be swiveled relative to the three-dimensional body 5, so that the borehole axis 9 and the longitudinal axis 28 of the central borehole 26 can enclose an angle with one another in the tensioning element 25.

The invention claimed is:

1. An assembly configured to attach to a support rod, the assembly comprising:
   a three-dimensional body comprising an upper surface, a lower surface opposite the upper surface, and a first wall at least partly disposed between the upper and lower surfaces;
   a channel having an axis and extending through the three-dimensional body, the channel configured to receive the support rod;
   a hole defined at least partially by the first wall, the hole extending through the three-dimensional body along a first direction that is transverse to the axis of the channel, the first wall including a resilient element positioned between the channel and the hole, the resilient element partly formed by two slots that extend into the first wall along a second direction toward the axis of the channel; and
   a bone fixation element configured to be received in the hole, the bone fixation element including a shaft that is configured to be inserted into a bone, the shaft being configured and sized to extend beyond the lower surface when the bone fixation element is received in the hole,
   wherein placement of the bone fixation element into the hole causes the resilient element to move to thereby clamp the support rod in the channel when the channel has received the support rod.

2. The assembly of claim 1, wherein the resilient element is hook-shaped.

3. The assembly of claim 1, wherein the channel is contracted by a portion of the resilient element so that the support rod can be snapped into the channel.

4. The assembly of claim 1, wherein the resilient element is integral with the three-dimensional body.

5. The assembly of claim 1, wherein the hole is conically shaped.

6. The assembly of claim 1, wherein the three-dimensional body comprises an internal thread formed around the hole.

7. The assembly of claim 1, wherein the hole has at least one conical longitudinal section with a conical angle ranging from 5 degrees to 25 degrees.

8. The assembly of claim 1, wherein the hole has at least one conical longitudinal section with a conical angle ranging from 8 degrees to 15 degrees.

9. The assembly of claim 1, wherein the hole is defined at least by a spherically concave shaped wall, and a spherical element is supported pivotably by the spherically concave shaped wall in the hole, wherein when the bone fixation element is tightened, the spherical element expands.

10. The assembly of claim 1, wherein the hole has a top conical longitudinal section and a bottom conical longitudinal section, wherein the top conical longitudinal section expands upwardly towards an upper end of the hole and the bottom conical longitudinal section expands downwardly towards a lower end of the hole.

11. The assembly of claim 1, wherein the bone fixation element is a bone screw comprising a head that is connected to the shaft.

12. The assembly of claim 11, wherein the three-dimensional body comprises an internal thread formed around the hole, and the head of the bone fixation element has an external thread that is configured to mate with the internal thread.

13. The assembly of claim 12, wherein a pitch of the external thread is between 0.1 and 3.0 mm.

14. The assembly of claim 11, wherein the head of the bone fixation element tapers conically inwardly.

15. The assembly of claim 14, wherein the head has a conical angle ranging from 5 degrees to 25 degrees.

16. The assembly of claim 1, wherein the three-dimensional body further comprises a second channel, and the hole is at least partially defined by a second wall, the second wall comprising a second resilient element, wherein when the bone fixation element is introduced into the hole, the second resilient element moves to clamp a second support rod.

17. The assembly of claim 1, wherein the bone fixation element includes a head that is connected to the shaft, the head is configured to abut the resilient element when the bone fixation is in the hole to press the resilient element against the support rod after the channel has received the support rod.

18. An assembly configured to attach to a plurality of support rods, the assembly comprising:
   a three-dimensional body comprising an upper surface, a lower surface opposite the upper surface, a first wall, and a second wall, each of the first and second walls including a fixed end disposed adjacent to and aligned with one of the upper and lower surfaces, and a free end spaced from the fixed end toward the other of the upper and lower surfaces, the fixed end being integral with the three-dimensional body;
   a first channel having a first axis and extending through the three-dimensional body, the first channel configured to receive a first support rod of the plurality of support rods;
   a second channel having a second axis and extending through the three-dimensional body, the second channel configured to receive a second support rod of the plurality of support rods;
   a hole positioned between the first channel and the second channel, the hole at least partially defined by the first wall and the second wall, the hole extending through the three-dimensional body, the first wall comprising a first resilient element positioned between the first channel and the hole, and the second wall comprising a second resilient element positioned between the second channel and the hole, wherein the free ends of the respective first and second walls are moveable relative to their respective fixed ends; and a bone fixation element configured to be received in the hole, the bone fixation element including a shaft that is configured to be inserted into a bone, wherein the shaft is configured and sized to extend beyond the lower surface when the bone fixation element is received in the hole, wherein placement of the bone fixation element into the hole causes 1) the free end of the first resilient element of the first wall to move to thereby clamp the first support rod in the first channel, and 2) the free end of the second resilient element of the second wall to move to clamp the second support rod in the second channel when the first channel has received the first support rod and the second channel has received the second support rod.

19. The assembly of claim 18, wherein an end of the first resilient element is hook-shaped.

20. The assembly of claim 18, wherein the first channel is contracted by an end of the first resilient element so that the first support rod can be snapped into the first channel.

21. The assembly of claim 18, wherein the hole is conically shaped.

22. An implantable device configured to join at least one connecting rod to a bone fixation element, the implantable device comprising:

a body including an upper portion and a lower portion;

an opening that extends from the upper portion of the body through the lower portion of the body, the opening configured to receive the bone fixation element;

a channel in the lower portion of the body, the channel configured to receive the at least one connecting rod; and a resilient member integral with the body and positioned so that a first portion of the resilient member communicates with the opening, and a second portion of the resilient member communicates with and is moveable relative to the channel;

wherein the at least one connecting rod is secured to the channel via the resilient member when the bone fixation device is inserted through the opening, and wherein the resilient member is formed by two slots in the body and is resiliently moveable in a first direction to permit the at least one connecting rod to be snapped into the channel and is resiliently moveable in a second direction by insertion of the bone fixation element into the opening so as to clamp the at least one connecting rod in the channel.

23. The implantable device of claim 22, wherein the opening is at least partially defined by a first wall, and the two slots extend into the first wall in a direction that is transverse to an axis defined by the channel.

24. The implantable device of claim 22, wherein the resilient member is hook-shaped.

25. The implantable device of claim 22, wherein the channel is contracted by at least a section of the resilient member, the resilient member configured and arranged so that the at least one connecting rod can be snapped into the channel.

26. The implantable device of claim 22, wherein the opening is conically shaped.

27. The implantable device of claim 22, wherein the opening is at least partially defined by a spherically concave shaped wall, and a spherical element is supported pivotably by the spherically concave shaped wall in the opening, wherein when the bone fixation element is tightened, the spherical element expands.

28. A device configured to attach a support rod to a bone fixation element, the device comprising:

a three-dimensional body including an upper portion and a lower portion;

a channel having an axis and extending through the lower portion of the three-dimensional body;

a hole extending through the upper and lower portions of the three-dimensional body, the hole positioned so as to extend orthogonally with respect to the axis of the channel; and a resilient tab integrally formed with the three-dimensional body, the resilient tab positioned between the channel and the hole, the resilient tab formed by two slots in the three dimensional body, wherein the resilient tab is resiliently moveable in a first direction to permit the support rod to be snapped into the channel and resiliently moveable in a second direction by insertion of the bone fixation element to clamp the support rod in the channel.

29. The device of claim 28, wherein the hole is at least partially defined by a first wall, and the two slots extend into the first wall in a direction transverse to the axis of the channel.

30. The device of claim 28, wherein the resilient tab is hook-shaped.

31. The device of claim 28, wherein the channel is contracted by a portion of the resilient tab, the resilient tab configured and arranged so that the support rod can be snapped into the channel.

32. The device of claim 28, wherein the hole is conically shaped.

33. The device of claim 28, wherein the hole is at least partially defined by a spherically concave shaped wall, and a spherical element that is supported pivotably by the spherically concave shaped wall in the hole, wherein when the bone fixation element is tightened, the spherical element expands.

34. A device configured to attach a support rod to a bone fixation element, the device comprising:

a three-dimensional body including an upper portion and a lower portion;

a channel having an axis and extending through the lower portion of the three-dimensional body, the channel configured to receive the support rod in a direction orthogonal to the axis;

a hole extending through the three-dimensional body, the hole positioned orthogonal to the channel, the hole configured to receive the bone fixation element; and a resilient tab integrally formed with the three-dimensional body, the resilient tab formed by two slots in the three dimensional body and resiliently moveable in a first direction to permit the support rod to be moved into the channel and resiliently moveable in a second direction by insertion of the bone fixation element to clamp the support rod in the channel.

35. The device of claim 34, wherein the hole is at least partially defined by a first wall, and the two slots extend into the first wall in a direction that is transverse to the axis of the channel.

36. The device of claim 34, wherein the resilient tab is hook-shaped.

37. The device of claim 34, wherein the channel is contracted by a portion of the resilient tab, the resilient tab configured and arranged so that the support rod can be snapped into the channel.

38. The device of claim 34, wherein the hole is conically shaped.

39. The device of claim 34, wherein the hole is at least partially defined by a spherically concave shaped wall, and a spherical element is supported pivotably by the spherically concave shaped wall in the hole, wherein when the bone fixation element is tightened, the spherical element expands.

\* \* \* \* \*